United States Patent [19]

Wilde et al.

[11] Patent Number: 4,987,037
[45] Date of Patent: Jan. 22, 1991

[54] GALVANIC COATING WITH TERNARY ALLOYS CONTAINING ALUMINUM AND MAGNESIUM

[75] Inventors: Bryan E. Wilde, Granville, Ohio; Michael K. Budinski, Pittsford, N.Y.

[73] Assignee: The Ohio State University, Columbus, Ohio

[21] Appl. No.: 279,500

[22] Filed: Dec. 5, 1988

Related U.S. Application Data

[62] Division of Ser. No. 75,591, Jul. 20, 1987, Pat. No. 4,826,657.

[51] Int. Cl.$^5$ .................................................. C23F 2/12
[52] U.S. Cl. .................................... 428/653; 427/431; 204/148; 204/197
[58] Field of Search ........................ 427/431; 428/653; 204/148, 197

[56] References Cited

U.S. PATENT DOCUMENTS 2,139,246  12/1938  Spitalar ............................ 420/546

Primary Examiner—Sam Silverberg
Attorney, Agent, or Firm—Frank H. Foster

[57] ABSTRACT

Galvanic protection of steel is provided by means of coupling thereto of ternary alloys of Al/2.5 to 4% wt. Mg, 0.5 to 35% wt. Si, and Al/2.5-4% wt. Mg, 0.5 to 3.5% wt. Ge with teachings of steel having either alloy coupled thereto, as well as the alloys per se. Also, a technique for determining alloys useful for the cathodic protection is presented including determining the critical cathodic protection potential for steel and the galvanic current and corrosion potential for candidate alloy compositions followed by coupling to the steel of one such alloy composition whose determined corrosion potential is lower than the critical corrosion potential for the steel in the corrosive environment in which protection is sought.

10 Claims, 9 Drawing Sheets

GALVANIC COATING WITH TERNARY ALLOYS CONTAINING ALUMINUM AND MAGNESIUM

This is a division of application Ser. No. 07/075,591, filed July 20, 1987, and issued May 2, 1989 as U.S. Pat. No. 4,826,657.

This invention relates to protection of steel from corrosion by certain essentially ternary alloys containing aluminum and magnesium, and includes not only the alloys for providing the protection, but also a procedure with determination of criteria for establishing which alloys are suitable and useful, as well as using the alloys for galvanic protective purposes and also an assembly of steel galvanically coupled to the alloy. More particularly, the invention concerns certain aluminum/magnesium/silicon and aluminum/magnesium/germanium essentially ternary alloys providing improved galvanic corrosion resistance for steel, their use to cathodically protect steel, and these alloys galvanically coupled to steel.

BACKGROUND

Zinc and other metal coatings have been in use for many years as an effective means of controlling the corrosion of steel. Due to the protective effect of galvanic coatings, the use of galvanized steel has increased markedly.

In recent years automobile manufacturers, designing lighter weight, corrosion resistant vehicles, have stimulated the use of galvanized steel. A drive to reduce the weight of vehicles calls for the use of high-strength, low-alloy steels with thinner wall thicknesses. The use of thinner sheet steel requires additional corrosion resistance providable through the use of galvanic coatings. Automobile manufacturers are also interested in the forming of coated sheet steel for auto body panels. Forming coated steel requires a relatively thin galvanic coating. Because of the relatively high galvanic and self corrosion of coatings of zinc per se, thick coatings have been necessary. To improve the formability of such protectively coated steel, the thick coating desirably should be replaced with a thin, more corrosion resistant coating with improved galvanic protective properties.

The use of galvanic coatings is increasing in other areas also, such as reinforcing bars for concrete structures. It has been documented that corrosion of steel rebar due to halide salts within the concrete is the basis for the formation of potholes and cracked concrete. Coating the steel with a high performance galvanic coating is one proposal to alleviate this problem.

It is obvious that the increasing use of galvanized steel puts great emphasis on the performance of galvanic coatings. Although pure zinc coatings adequately protect steel, they have several drawbacks including:

(1) The widely differing electrode potentials between zinc and steel [$-1.05$ Vsce, (Volts versus a saturated calomel reference electrode), and $-0.69$ Vsce respectively in aerated salt water solutions] result in excessive galvanic corrosion, where the zinc actually overprotects the steel.

(2) Hydrogen gas evolution may occur due to the large cathodic overvoltage. In some instances this may impair the mechanical properties of steel. An example of this is a steel reinforcement bar in concrete.

(3) Painted galvanized steel experiences rapid paint undercutting and delamination due to the excessively large cathodic overvoltage and corrosion product wedging.

(4) The self corrosion rate of zinc is relatively high in certain environments.

The aforementioned problems with zinc coatings are from a corrosion standpoint. Other concerns with coatings in general are: weldability, spangle (grain size), formability, paintability, and brittle metallic layers.

From the foregoing, it is apparent that opportunity exists for considerable improvement over the use of pure zinc coatings for corrosion protection of steel.

The corrosion of pure aluminum coatings has received study. Salama and Thomason (J. Petroleum Tech., Nov., p. 1929, 1984) have found that flame sprayed aluminum (FSA) coatings satisfactorily protected steel in sea water. P. 0. Gartland (Paper 299, NACE Corrosion 86 Conference, Houston, Texas, March 17-21, 1986) compared flame sprayed aluminum, and aluminum-3 weight percent magnesium coatings in sea water. There seemed to be little difference between the performance of these two coatings. They both afforded corrosion resistance 10 to 15 times greater than zinc. Thomason (Materials Performance, p. 20, March, 1985) showed that FSA coatings will protect steel. However, if large areas of the coating are damaged, corrosion of the steel may ensue due to the lack of throwing power of aluminum coatings.

Atmospheric corrosion studies by Townsend and Zoccola (Materials Performance, p. 12, Oct., 1979) indicate that the passivity of aluminum impairs its ability to protect edges. In marine environments, however, the aluminum reportedly protected the edges of the steel. It is believed that the chloride ions keep the aluminum in an active state.

Aluminum is often used as a sacrificial anode for cathodic protection. Reboul et. al. (Corrosion, Vol. 40, No. 7, p. 366, 1984) studied the effect of zinc, indium, tin and mercury on the activation of aluminum. These elements are added to disrupt the aluminum oxide film, thereby activating the aluminum. They have shown that only elements in solid solution are capable of activating the aluminum. D. S. Keir et al (J. Electrochem. Soc., Vol. 116, No. 3, 1969) investigated the addition of bismuth, zirconium, magnesium, silver, cobalt, nickel, and iron to an aluminum-0.1 weight percent tin alloy. They found that only elements that were soluble in the alloy would effect the galvanic current.

It has also been noted that the paintability of aluminum coatings is superior to any zinc or zinc alloy coating (H. Leidheiser, Jr., Corrosion, Vol., 38, No. 5, p. 189, 1983). The reason for this lies in the fact that aluminum is a poor catalyst for the oxygen reduction reaction. The oxygen reduction reaction plays a vital role in the cathodic delamination of paint films.

The present disclosure teaches a unique electrochemical technique for the development of galvanic coating alloys. Through its use, several new galvanic coating alloys containing aluminum and magnesium with improved corrosion resistance have been provided, as will be apparent from what follows.

SUMMARY STATEMENT OF THE INVENTION

Steel, e.g. DQSK steel, was protected from galvanic corrosion in an aqueous salt environment by coupling the steel with an alloy selected from the group of alloys consisting essentially of (i) 2.5 to 4 percent by weight of magnesium, 0.5 to 3.5 weight percent of silicon, and a balance of aluminum, and (ii) 2.5 to 4 percent by weight of magnesium, 0.5 to 3.5 weight percent of germanium, and a balance of aluminum. Desirably, the coupling is with the alloy as a coating adhering to the steel, and preferably the Al/Mg/Si alloy contains about 3 to 3.5 percent by weight of magnesium and 0.75 to 1.25 percent by weight of silicon, and the Al/Mg/Ge alloy contains about 3 to 3. percent by weight magnesium, 1 to 3 percent by weight of germanium.

The invention includes the manufacture, or assembly, of steel coupled, desirably coated, with the alloy. The invention also teaches the alloy composition.

The invention additionally provides a method for determination of a metal alloy composition for galvanic protection of steel (other than stainless steels), and the providing of galvanically protected steel by (a) placing a specimen of the steel, generally immersed, in the environment in which protection is to be provided and while within that environment determining its critical cathodic protection potential, (b) preparing or otherwise fabricating in bulk form a plurality of alloy specimens including those of varied compositions in which alloy components have been increased in incremental amounts, (c) placing these specimens individually in the same environment used to determine the critical cathodic protection potential of the steel and, while therein, measuring for each its galvanic current and corrosion potential at a time when corrosion of each has reached a substantially steady state rate, and subsequently coupling to the steel of an alloy of a composition which in step (c) provided a determined corrosion potential lower than the critical cathodic protection potential for the steel as determined in step (a).

BRIEF DESCRIPTION OF THE DRAWINGS

In the included drawings, a number of the figures present in schematic-like fashion various apparatuses, cell configurations and circuitry; other set-ups and the like, with it believed readily apparent from applicants, presented figures and disclosure to one of ordinary skill in the art how to assemble and provide the specific item illustrated in the particular figure. Accordingly.

DETAILED DESCRIPTION OF THE INVENTION

Figure 2:
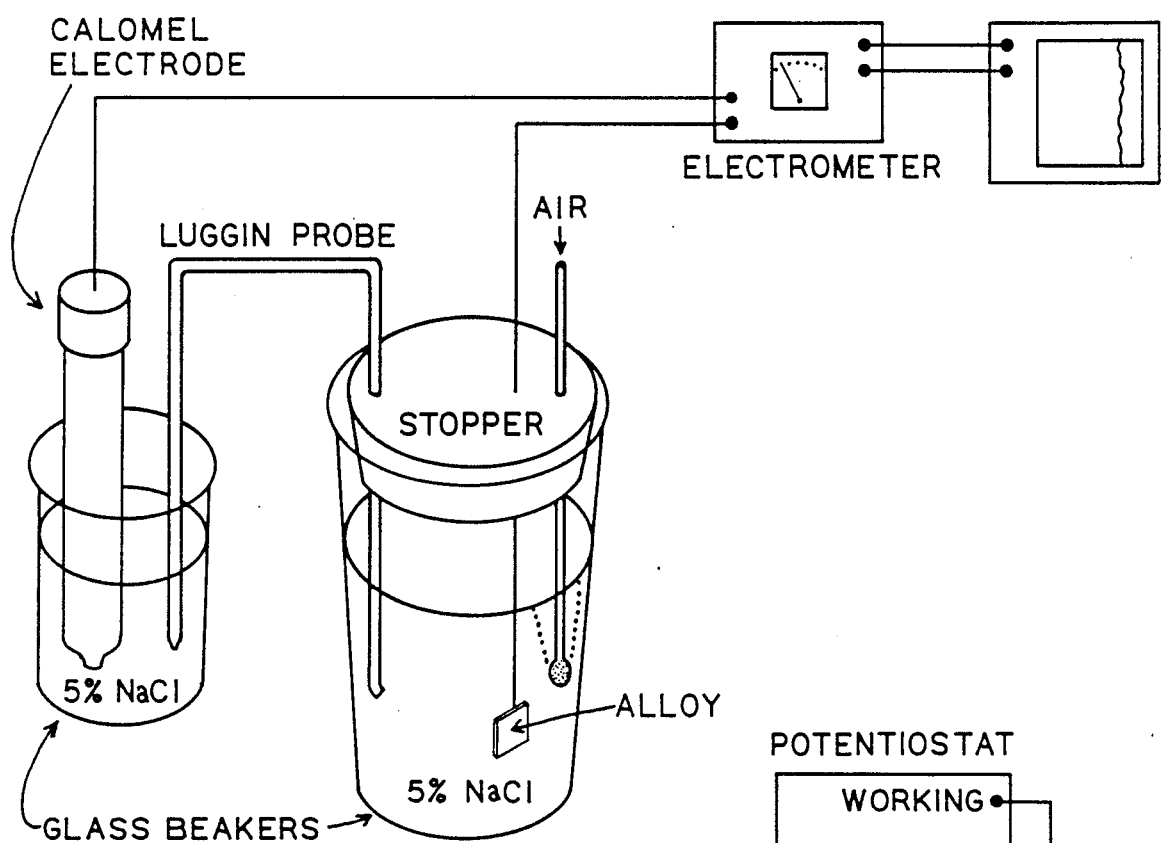
FIG. 2 presents a corrosion cell configuration for open circuit anode potential measurements.

The present invention utilizes an approach and technique as follows: Bulk alloys, rather than actual coatings, were used to determine useful and optimal composition. The invention determined the critical cathodic protection potential, which is a new criterion for the development of galvanic coatings. This is believed to not have been reported previously in the literature. This criterion was determined under conditions that mimic the environment (e.g. salt spray). It is important to note that the critical cathodic protection potential is valid only under conditions at which it was determined, e.g. continuous immersion in aerated 5% NaCl solution at 30 C.

The solution potential, galvanic corrosion current and coupled potential versus composition maps are also determined and apparently are new to the galvanic coating technology practices. This new information dictates what alloy compositions will cathodically protect steel and the optimal alloy composition. For the screening of potential galvanic coating alloys the approach and techniques reported herein are quite useful. In comparison to such tests as the ASTM B 117 salt spray test, this approach is less time consuming and gives quantitative data.

The polarization work here is rather unique since very little polarization work has been reported in the literature on galvanic coating alloys. In general, the current densities associated with the polarization of zinc and zinc alloys are several orders of magnitude higher than those of aluminum.

Through the invention, it was possible to make evaluations as to certain ternary alloys which are useful and will perform well as galvanic coatings on steel. The following TABLE I lists two particularly promising alloys for such a purpose.

TABLE I

| PROMISING GALVANIC COATING ALLOYS | | | |
|---|---|---|---|
| ALLOY COMPOSITION | CORROSION Rate uA/sq cm | GALVANIC CURRENT A | COUPLED POTENTIAL Vsce |
| Al-3Mg-1Ge | 3 | 85 | −0.77 |
| Al-3Mg-1Si | 15 | 90 | −0.765 |

In general, the determined useful ternary alloy is selected from the group of alloys consisting of (i) 2.5 to 4 percent by weight of magnesium, 0.5 to 3.5 percent by weight of silicon and a balance of aluminum, (ii) 2.5 to 4 percent by weight of magnesium, 0.5 to 3.5 percent by weight of germanium and a balance of aluminum. Particularly preferred are the alloy compositions set forth in the preceding TABLE I. Also preferred, as apparently being optimum are Al/about to 3.5 % wt, Mg/about 0.75 to 1.25 % wt. Si, and Al/about 3 to 3.5 % wt Mg/about 1 to 3 % wt. Ge.

The approach taken in the invention provides for the determination of a coating composition from a corrosion standpoint by means of continuous immersion. The procedure was:
1. Determination of the critical cathodic potential required for effective protection of steel (the substrate). This potential was used as a criterion for galvanic coating alloy development.
2. Fabrication of bulk ternary coating alloys and measurement of the corrosion potential as a function of composition for each of the alloy systems. The resultant potential vs. composition maps are basically a galvanic series for each alloy system.
3. Perform zero resistance ammeter tests to determine the galvanic current and coupled potential for each of the alloys. A 3.7:1 area fraction steel to coating alloy relation was used. Graphs of coupled potential and galvanic current as a function of alloy composition were plotted.
4. Using the criterion developed in step 1, the optimal coating compositions were determined from a galvanic corrosion standpoint. Polarization curves of the optimal alloys were then obtained to determine the self corrosion rate and polarization behavior of the alloy.
5. The optimal coating will protect steel to the critical cathodic overpotential, transfer minimal but adequate galvanic current and have a low self corrosion rate.

It is believed to be well accepted in the cathodic protection art that simulated evaluations using electrochemical methods are highly useful to determine and simulate actually useful galvanic coatings. It is asserted that as taught herein, those determinations and simulations provided to teach the invention, do mimic and do provide teachings highly indicative of the utility of the invention in the cathodic protection art.

Although the illustrative simulations include data collected when the steel and ternary alloys are coupled electrically by means of a wire and an electrolytic solution (e.g. 5% aqueous NaCl), such a coupling could just as well for end utility be an actual adherent coating of the alloy on the substrate (i.e. steel). It should be recognized that the corrosion performance of steel and galvanic alloys is very similar in solution of NaCl in the concentration range of 3.5 to 5% by weight. Such ternary alloys are contemplated as applicable to steel as coatings by at least one or more of the following techniques of electroplating, flame spraying, hot dipping, sheradizing, and the like.

DETERMINATION OF THE CRITICAL CATHODIC PROTECTION POTENTIAL

Figure 1:
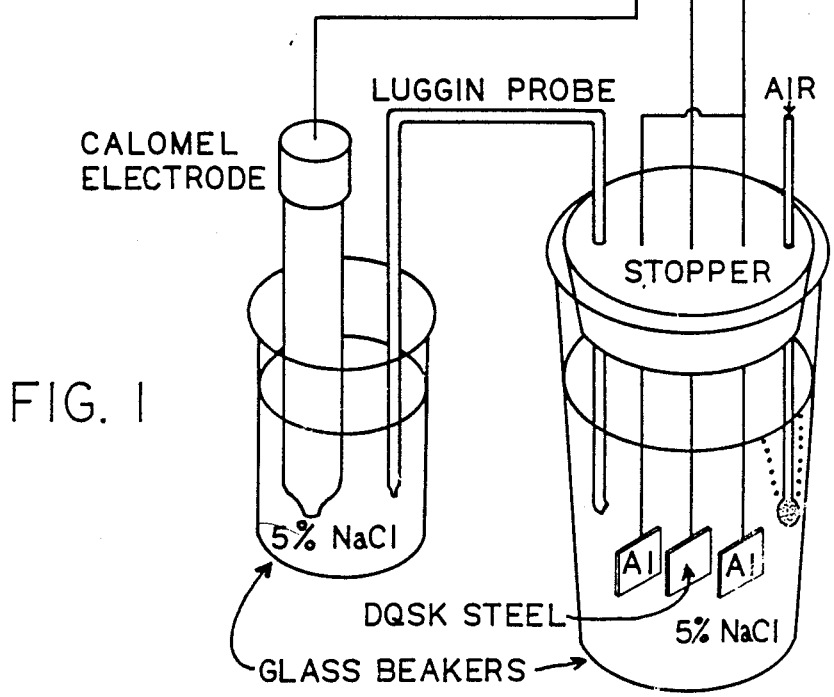
FIG. 1 illustrates an apparatus set-up for the determination of the critical cathodic potential of DQSK steel.

Paddle specimens of steel with known surface area were exposed to a 5 weight percent sodium chloride solution, at 25 C, using the system illustrated in FIG. 1. The entire unit was enclosed in an air thermostat, which controlled the temperature to ±1° C. A given volume of solution was introduced and saturated with air at a constant flow rate of 100 ml/min. The potential of the steel was controlled at the chosen value with a Wenking TS 3 potentiostat. Auxiliary electrodes of 1100 grade aluminum were located on either of the steel. All potentials were measured with reference to a saturated calomel electrode, with no correction for junction potentials.

Specimens were exposed for various periods, then removed from the solution. Because the corrosion products were in the form of rust ($Fe_2O_3$) all of the products from the test beaker were dissolved in warm, inhibited 25 volume percent HCl (inhibited with Rhodamine B). In separate tests, this procedure failed to produce any corrosion of the steel during descaling. The total iron corrosion product dissolved, in 25 volume percent HCl, was made up to 1000 ml volume in a standard flask. The iron content of the solution was measured using a Perkin-Elmer Atomic Absorption Spectrophotometer with a specific iron electron gun.

Corrosion rates were calculated using the following relationship $$mpy = \frac{534W}{DAT}$$

where W is the total weight of iron corrosion product found (mg) after exposure time T (hr). D is the density of carbon steel (7.86 g/cc) and A ($in^2$) is the area of the original paddle specimen in square inches.

All solutions were made using doubly deionized water and reagent grade chemicals.

CORROSION POTENTIAL MEASUREMENTS

The corrosion potential for each of the specimens was measured in air saturated 3.5 weight percent sodium chloride solution. This solution models road salt, sea water and salt spray conditions. The solution was air saturated in order to further model these conditions. Each specimen was prepared for immersion by degreasing in acetone and sanding with 400 grit abrasive. The corrosion cell used is shown in FIG. 2. All potential measurements were made relative to a saturated calomel electrode (sce) via a Keithly 602 electrometer. A strip chart recorder, connected to the electrometer's 1× analog output, was utilized to detect a steady-state solution potential. In the case of the specimens mounted in epoxy, the edges between the specimen and the epoxy were sealed with Miccromask (Pyramid Plastics Inc., Hope, Arkansas 71801), an electroplating lacquer. A Teflon (Du Pont Co., Wilmington, Del.) compression gasket and threaded rod were used to mount the threaded specimens.

ZERO RESISTANCE AMMETER MEASUREMENTS

Figure 3:
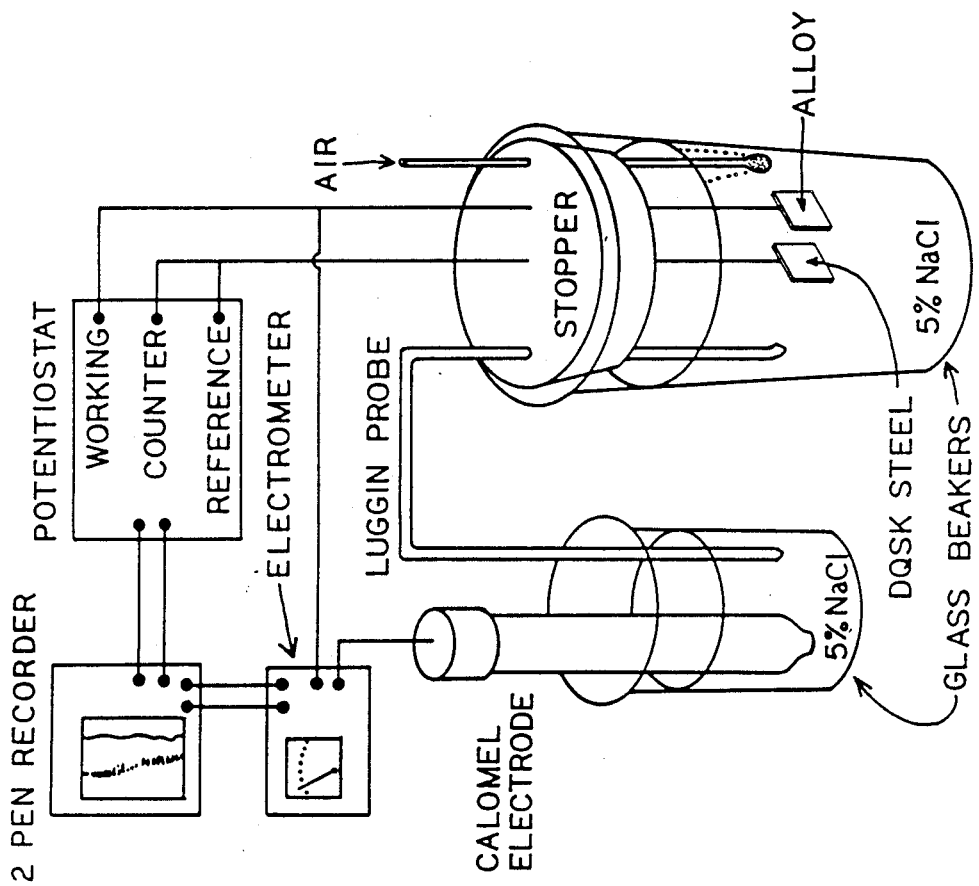
FIG. 3 shows a zero resistance ammeter set-up for determination of galvanic currents.

To measure the current transferred through a galvanic couple, a zero resistance ammeter was employed. A schematic diagram of the circuit setup along with the corrosion cell is shown in FIG. 3. A Wenking TS 3 potentiostat, a Kiethly 602 electrometer and an Esterline Angus dual pen strip chart were used to detect galvanic current and coupled potential as a function of time. Sample preparation involved degreasing the specimens in acetone and sanding them with 400 grit abrasive. In order to maintain a 3.7:1 area fraction between the steel and the alloy, Miccromask electroplating lacquer was used to mask the specimens.

The corrosion cell contained 250 ml of 3.5 weight percent sodium chloride solution. Air was bubbled through the solution at a rate of 35 ml/min. The exposed areas faced each other and the distance between areas was ⅜ inch. The potential measurements were made relative to a saturated calomel electrode, with no correction for junction potentials.

Typically, steady state current and potential measurements were achieved between 24 and 48 hours.

POLARIZATION CURVES

Figure 4:
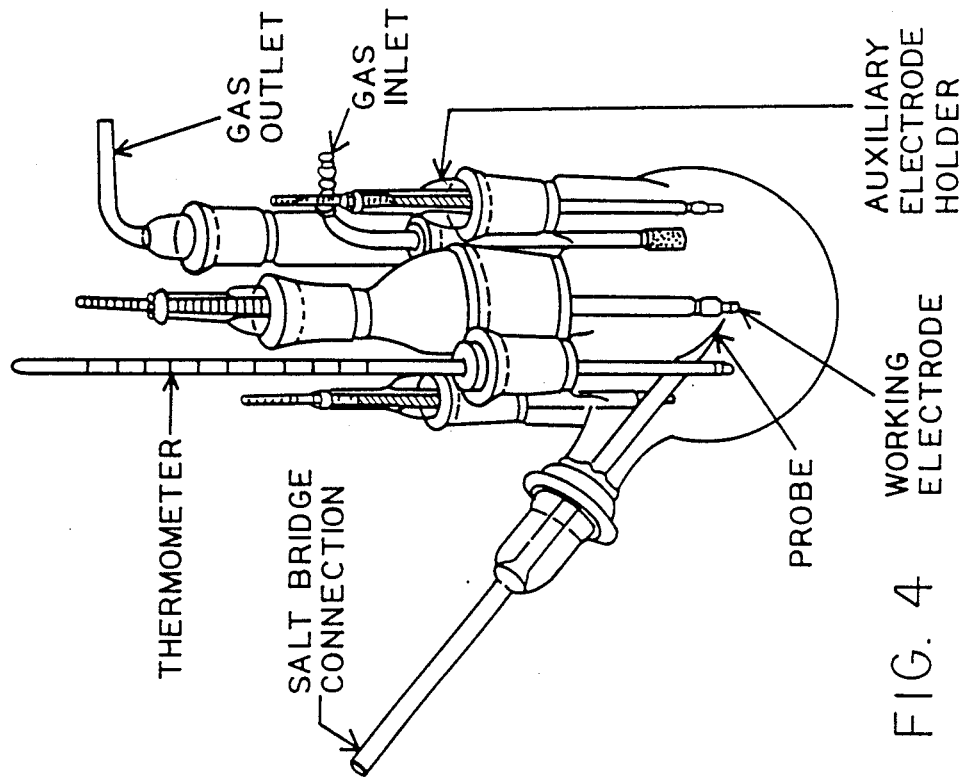
FIG. 4 illustrates a corrosion cell used for polarization studies, FIG. 5 provides a data plot of corrosion rate of DQSK steel in air saturated 5.0% sodium chloride solution at 25 C as a function of time, FIG. 6 provides a data plot of steady state corrosion rate of DQSK steel in aerated 5.0% sodium chloride solution at 25 C as a function of cathodic potential.

The metals and alloys of particular interest were subjected to potentiostatic measurements in order to obtain polarization curves. The corrosion cell used to make these measurements is shown in FIG. 4. The solution used for the tests was 3.5 weight percent sodium chloride saturated with air (45 ml/min). The test cell held 1000 ml of solution, and was maintained at a constant temperature of 25 C. During specimen immersion, the solution was purged with oil-free breathing air. The samples were prepared by degreasing in acetone and sanding with 400 grit abrasive. Specific areas were masked off using Miccromask. Exposed areas were measured to within ±0.002 sq. cm.

Upon specimen immersion, the corrosion potential of the specimen was recorded as a function of time using a Keithly 602 electrometer and a Hewlett Packard strip chart recorder. Steady state corrosion potentials were typically achieved within 4 to 8 hours. After steady state was reached, the specimens were polarized with a Wenking TS 3 potentiostat using a 1 square centimeter platinum counter electrode facing the specimen. A scan rate of 25 millivolts in 3 minutes was maintained. Cathodic and anodic polarization curves were run as separate events.

EXAMPLE

The steel used for this example was drawing quality semi-killed (DQSK) steel supplied by the U.S. Steel Co., Pittsburg, Pa. The steel was in the sheet form, 0.0255 inches thick. The average ASTM grain size of the steel was 7. This is a typical steel used for auto body panels. Since one application of the invention is a development of improved galvanic coatings for automobiles, this choice of steel is logical and especially illustrative. The example could just as well employed another steel, e.g. carbon steel or low alloy steel, and similar illustrative results would be obtained. The only steel to which the invention is not particularly applicable are those steels customarily designated to be stainless steels and the like, with such steels and their alloys not normally provided with galvanic protection.

The aluminum alloys were made by melting measured amounts of the constituent elements in an alumina or graphite crucible in a 10kW induction furnace. The elemental metals used in the alloys were reagent grade and were obtained from commercial sources. Twenty gram melts were made and cast into a cold copper mold to produce cylindrical ingots ½ inch in diameter ×2 inches long. Upon casting, the alloys solidified within 1 second.

The alloying elements added to the molten aluminum were wrapped in commercial aluminum foil, to avoid excessive oxidation. Visual and optical inspection indicated no apparent porosity due to hydrogen gas, therefore, the melts were not degassed.

Specimens were carefully machined from the ingots. The specimens, being cylindrical in shape, were ½ inch in diameter and ½ inch long. One end of the cylinder was internally threaded for ⅜ inch with ¼-20 NC threads.

THE CRITICAL CATHODIC PROTECTION POTENTIAL

Figure 5:
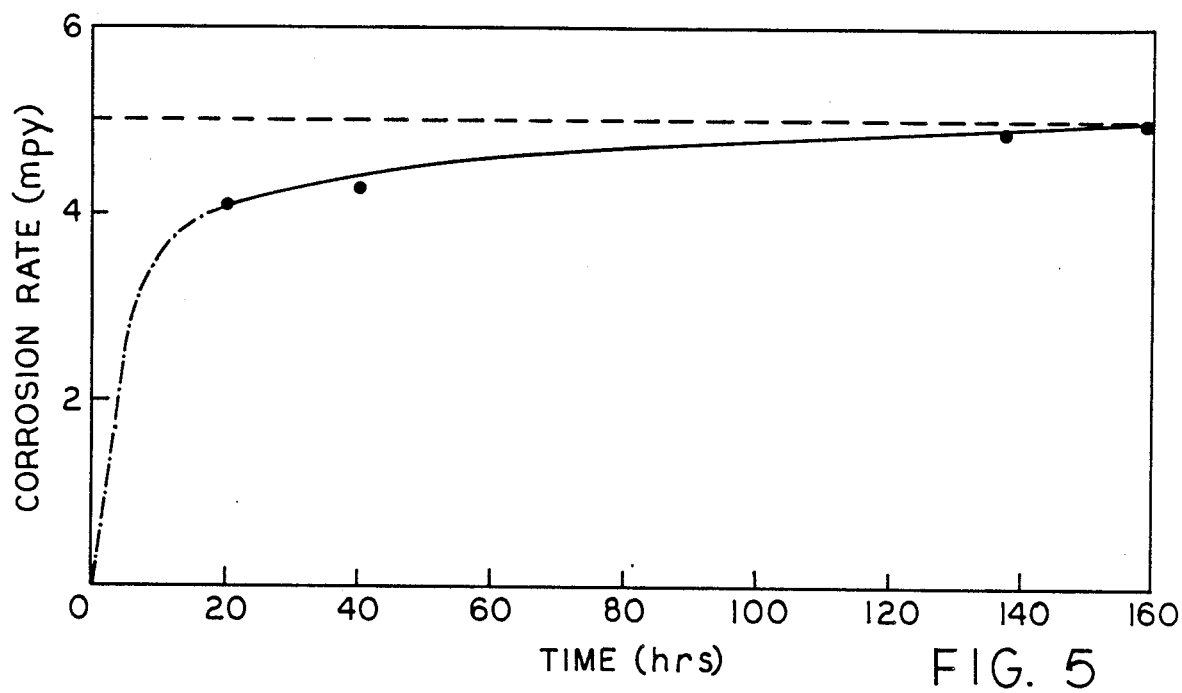

To insure that the steel was corroding at steady state, a series of tests were conducted, over a 200 hour test period with no applied potential. Samples were taken at various intervals over the 200 hours, and the results are shown in FIG. 5. It is clear that a minimum 160 hour exposure time was necessary to achieve steady state. All subsequent tests were conducted for 160 hours.

Figure 6:
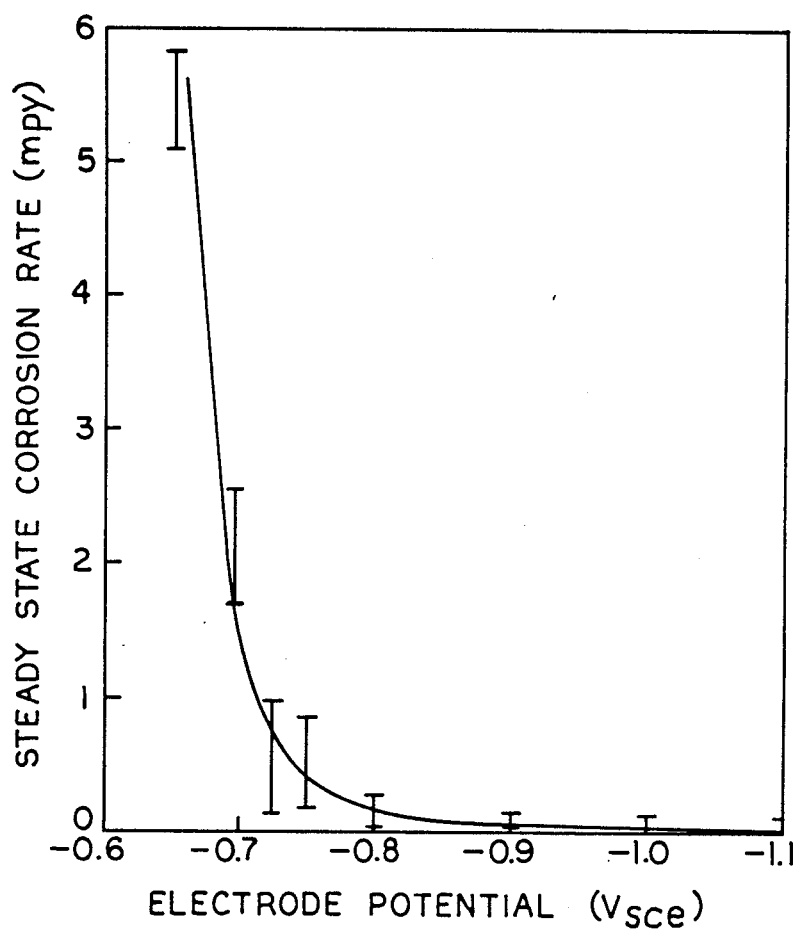

The influence of applied cathodic potential on the corrosion rate of DQSK steel is shown in FIG. 6. The error bars illustrate the variability of the data. From the figure, it is clear that a corrosion rate of less than 1 mil per year (mpy) can be achieved with an applied potential of 0.725 Vsce. As the applied cathodic potential was increased, the corrosion rate further decreased—essentially reading zero at −1.1 Vsce. It has been noted that effective cathodic protection (e.g. less than 1 mpy) may be achieved at potentials less negative than commonly accepted values. For example: the critical cathodic potential for steel in beer was found to be about −0.700 Vsce, and the critical cathodic potential for steel in simulated concrete environments was also found to be less negative than the commonly accepted-0.850 V (vs. copper/copper sulfate criterion).

The curve in FIG. 6 thus establishes that DQSK steel will receive adequate cathodic protection in aerated 5.0 wt/o sodium chloride solutions at potentials in the range of −0.725 to −0.750 Vsce. This curve also reveals the reversible potential for the cathodic partial process. This potential is in the range of 0.850 to −0.950 Vsce where the corrosion rate is zero.

SOLUTION POTENTIALS OF ALLOYS

The corrosion potential was determined for each of the alloys of the invention. Corrosion potential maps were made as a function of alloy composition. These corrosion potential maps are actually galvanic series for each of the alloy systems. Although they give no information about the degree of galvanic corrosion, they indicate the composition range in which cathodic protection may be achieved if the steel were galvanically coupled to a particular alloy.

Figure 7:
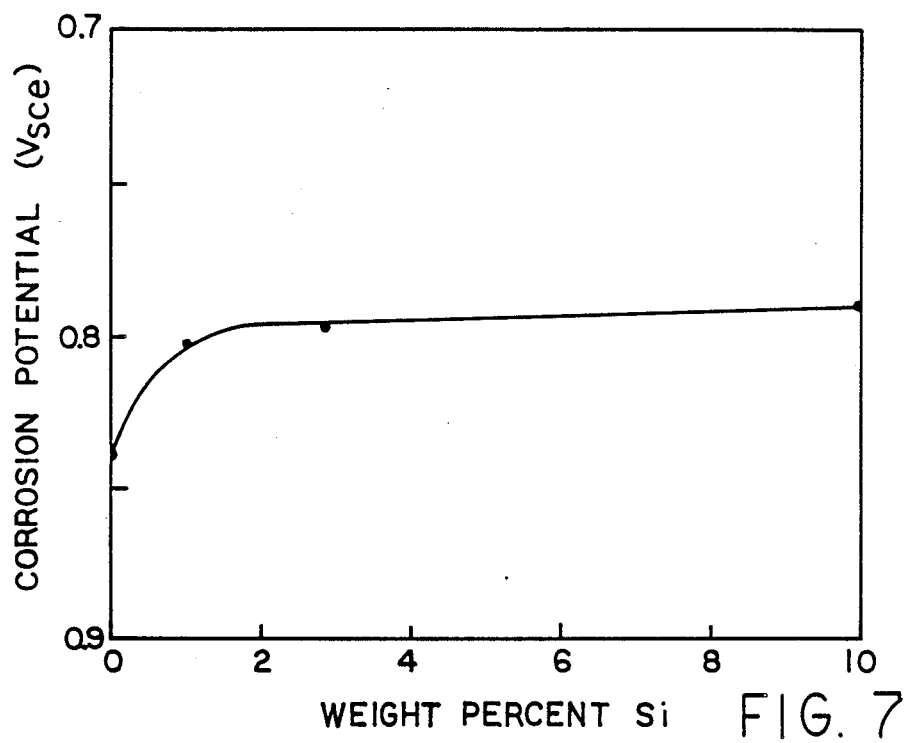
FIG. 7 presents a data plot of solution potential of aluminum-silicon alloys as a function of silicon content in air saturated 3.5% sodium chloride solution at 25 C.

Previous research by Reboul et. al. (Corrosion, Vol. 40, No. 7, p. 366, 1984) and the inventors, research indicate that the solution potentials of aluminum alloys are only affected by alloying elements in the solid solution range. This may be observed in the Al/Si system shown in its corrosion potential map in FIG. 7. At compositions greater than the solid solution limit, the solution potentials remain rather constant. All compositions of the Al/Si alloys investigated offered cathodic protection.

Figure 8:
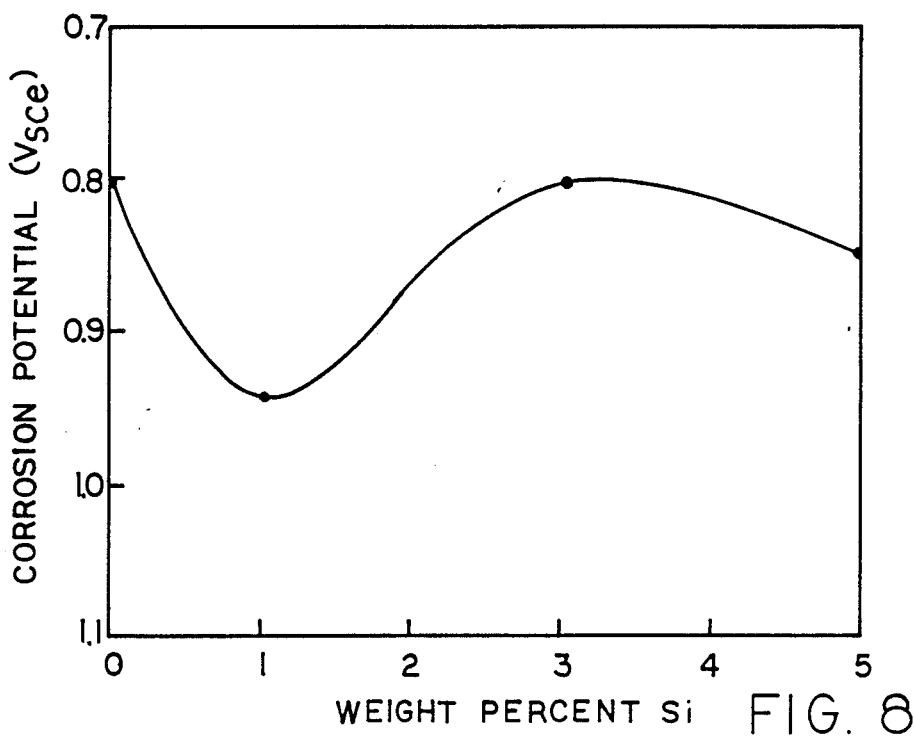
FIG. 8 presents a data plot of solution potential of Al-3 Mg-Si alloys as a function of silicon content in air saturated 3.5% sodium chloride solution at 25 C, FIG. 9 provides a plot of solution potential of Al-3 Mg-Ge alloys as a function of germanium content in air saturated 3.5% sodium chloride solution at 25 C.
Figure 9:
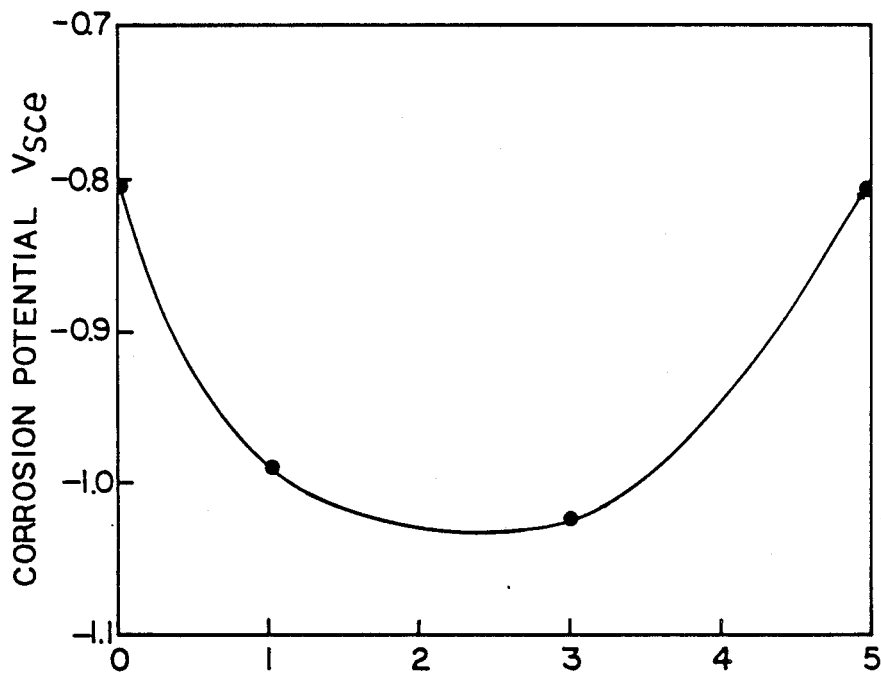

The effect of Si and Ge alloy additions on the corrosion potential of Al-3 Mg are shown in FIGS. 8 and 9. In general, the presence of magnesium tends to change the electrode potentials to more electronegative values.

ZERO RESISTANCE AMMETER (ZRA) DETERMINATIONS

ZRA data gives a more complete picture of the degree of galvanic corrosion. The galvanic series (i.e. solution potentials) only indicate which alloy compositions are cathodic to steel.

Figure 10:
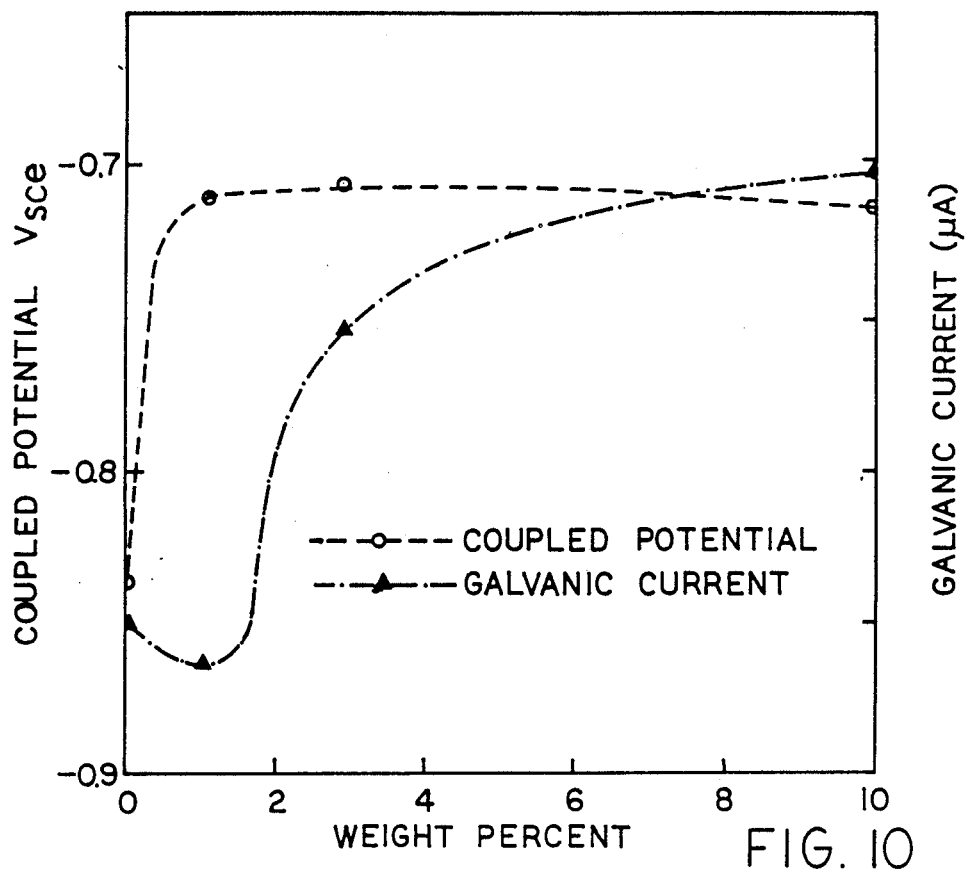
FIG. 10 presents a data plot of galvanic current and coupled potential for Al/Si alloys coupled to steel in aerated 3.5% NaCl solution.
Figure 12:
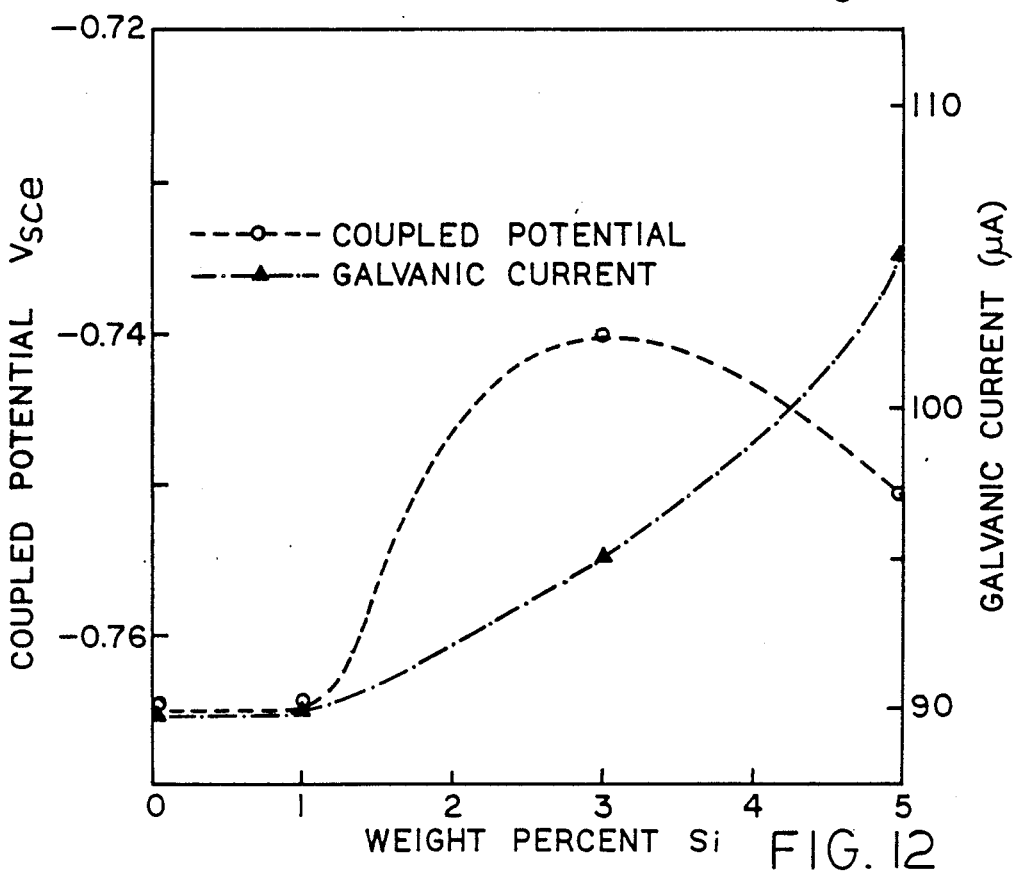
FIG. 12 presents a data plot of galvanic current and coupled potential for Al-3Mg/Si alloys coupled to steel in aerated 3.5% NaCl solution, FIG. 13 provides anodic and cathodic polarization curves for DQSK steel in air saturated 3.5% NaCl solution at 25 C, FIG. 14 provides the anodic polarization curve for aluminum in air saturated 3.5% solution at 25 C, FIG. 15 provides the anodic polarization curve for Al-3Mg in air saturated 3.5% NaCl solution at 25 C, FIG. 16 provides the anodic polarization curve for Al-3Mg-1Si in air saturated 3.5% sodium chloride solution at 25 C, and FIG. 17 provides the anodic polarization curve for Al3Mg-1Ge in air saturated 3.5% NaCl solution at 25 C.

FIGS. 10 and 12 show the galvanic current and coupled potential for aluminum and aluminum-magnesium alloys. As a general trend it may be noticed that alloy additions greater than solid solution limit tend to be detrimental (in terms of increased galvanic currents).

The galvanic current for aluminum-silicon alloys may be seen in FIG. 10. This curve shows that alloy additions of silicon to aluminum greater than 1 weight percent give rise to higher galvanic currents than pure aluminum. This curve is significant to industry as silicon in concentrations of 3 to 10 weight percent are often present in aluminum coated steel. The silicon is added to reduce the very brittle Fe/Al intermetalic layer that forms during hot dipping. The coupled potentials of Al/Si alloys with 1 weight percent or more silicon are more noble than the critical cathodic protection potential of −0.725 Vace. This explains why silicon containing aluminum coatings may not be protective in certain environments.

The addition of 3 weight percent to magnesium appears to have little effect on the galvanic current of aluminum. The magnesium addition causes the coupled potential to change to slightly more cathodic potentials. Magnesium was added to counteract the deleterious effects produced by an element, such as silicon.

Figure 11:
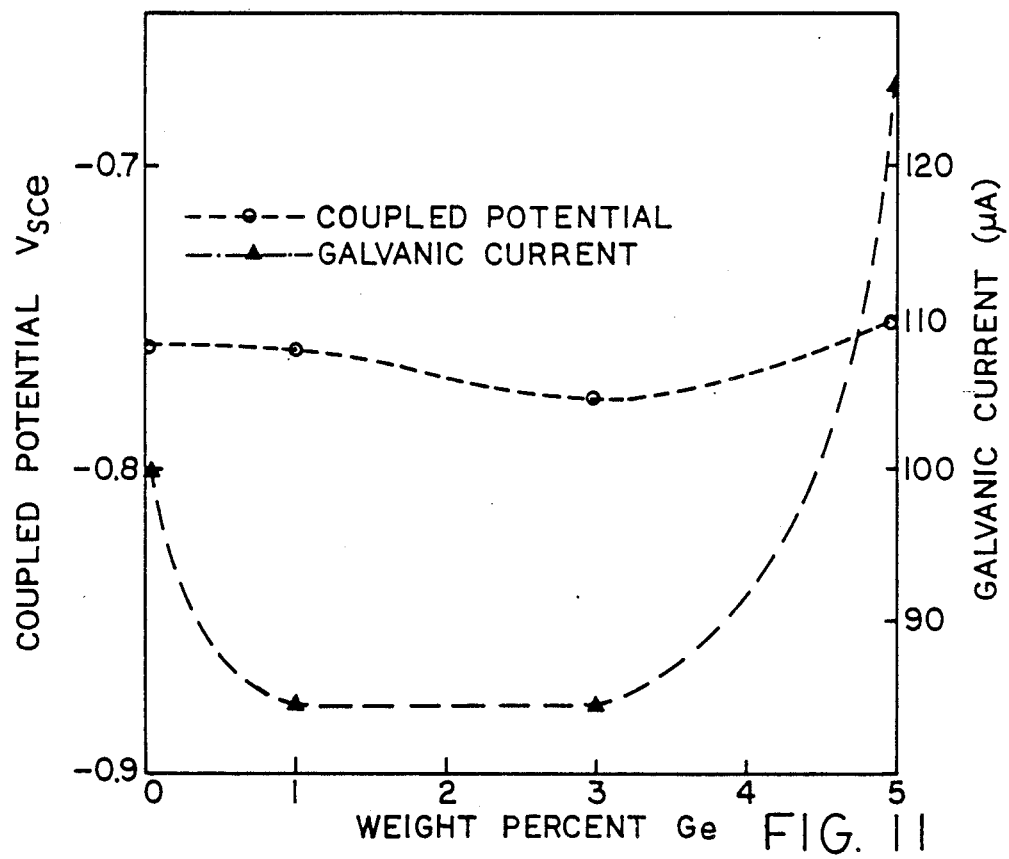
FIG. 11 presents a data plot of galvanic current and coupled potential for Al-3Mg/Ge alloys coupled to steel in aerated 3.5% NaCl solution.

FIG. 11 shows that additions of germanium in the 1 to 3 weight percent range have a beneficial effect on the galvanic corrosion on Al-3 Mg alloys. The coupled potential of −0.775 Vsce and the low galvanic current of 70 microamps of Al-3Mg alloys with 1 to 3 percent Ge makes these alloy compositions optimal.

FIG. 12 shows that the addition of silicon to Al-3 Mg changes the coupled potential to more cathodic values; in the range of −0.750 Vsce. The galvanic current increases with increasing silicon content. It is possible that the corrosion properties of silicon containing aluminum coatings may be improved through the addition of magnesium.

POLARIZATION DETERMINATIONS

Figure 13:
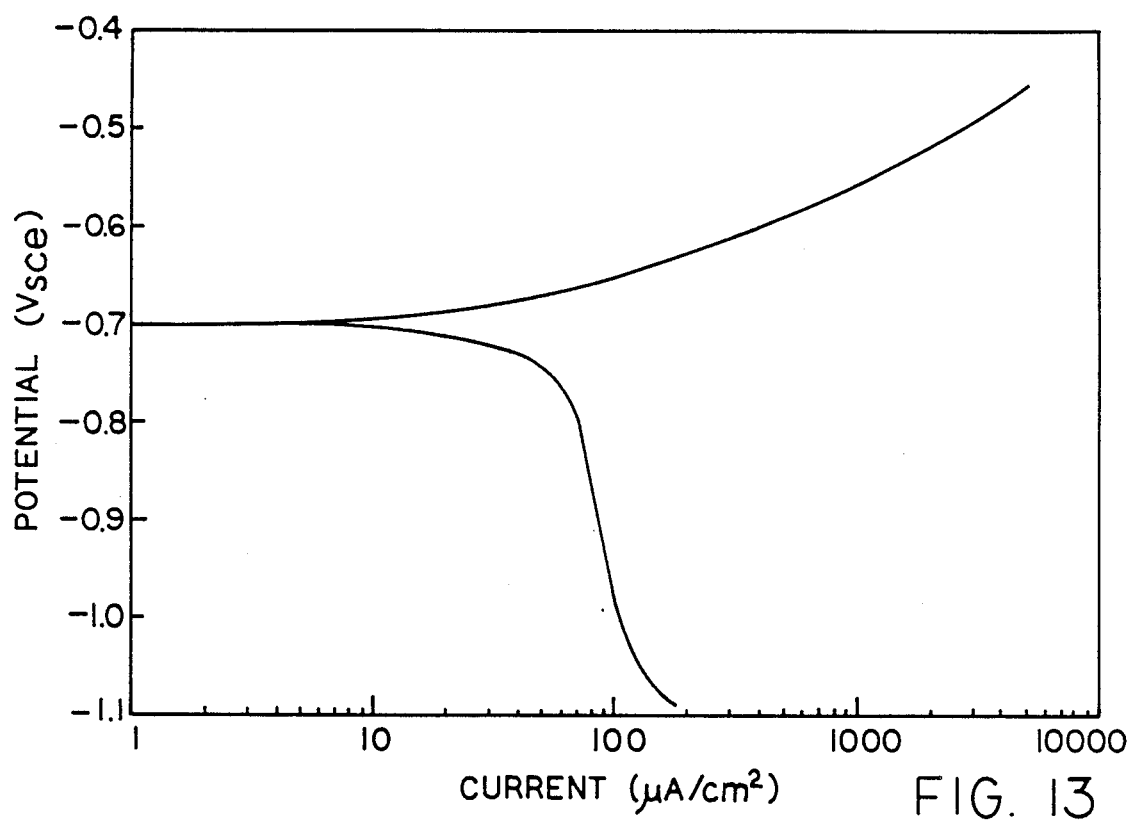

Polarization data for the alloys of concern were determined to give insight on how polarization affects galvanic coupling. FIG. 13 shows cathodic and anodic polarization curves for DQSK steel. Through Tafel slope extrapolation, the estimated corrosion current for DQSK steel in aerated salt water is on the order of 100 microamps/sq cm. The shape of the cathodic curve is of particular interest as it shows a limiting current density due to the diffusion controlled oxygen reduction reaction. This limiting current density plays a vital role in the magnitude of the galvanic current.

Corrosion current densities were calculated through linear polarization (M. Stern, A. L. Geary, J. Electrochem. Soc., Vol. 105, p. 638, 1958) using the following equation:

$$\frac{E}{\Delta I_{appl}} = \frac{B_a B_c}{2.3 I_{corr} (B_a + B_c)}$$

where $E/I_{appl}$ is the slope of the polarization curve for the first 10 mV. Both the anodic Tafel slope $B_a$, and the cathodic Tafel slope, $B_c$, were assumed to be equal to 0.12 V/decade. Stern and Weisert (Proc. ASTM, Vol. 59, p. 1280, 1959) have shown that this assumption results in a corrosion rate that differs from the actual corrosion rate by no more than a factor of three. $I_{corr}$ is equal to the corrosion rate. The polarization behavior of aluminum and aluminum alloys is quite different than that of zinc and zinc alloys. The point of galvanic coupling for aluminum alloy/steel galvanic couples tends to be at the point where the anodic polarization curve for the aluminum alloy, in the transpassive regime intersects the cathodic curve for steel. Potentiostatic measurements were conducted on Al, Al-3 Mg. Anodic polarization curves also were determined for the following coating alloys: Al-3Mg-1Ge and Al-3Mg-1Si. Corrosion current densities for these alloys was estimated using linear polarization.

Figure 14:
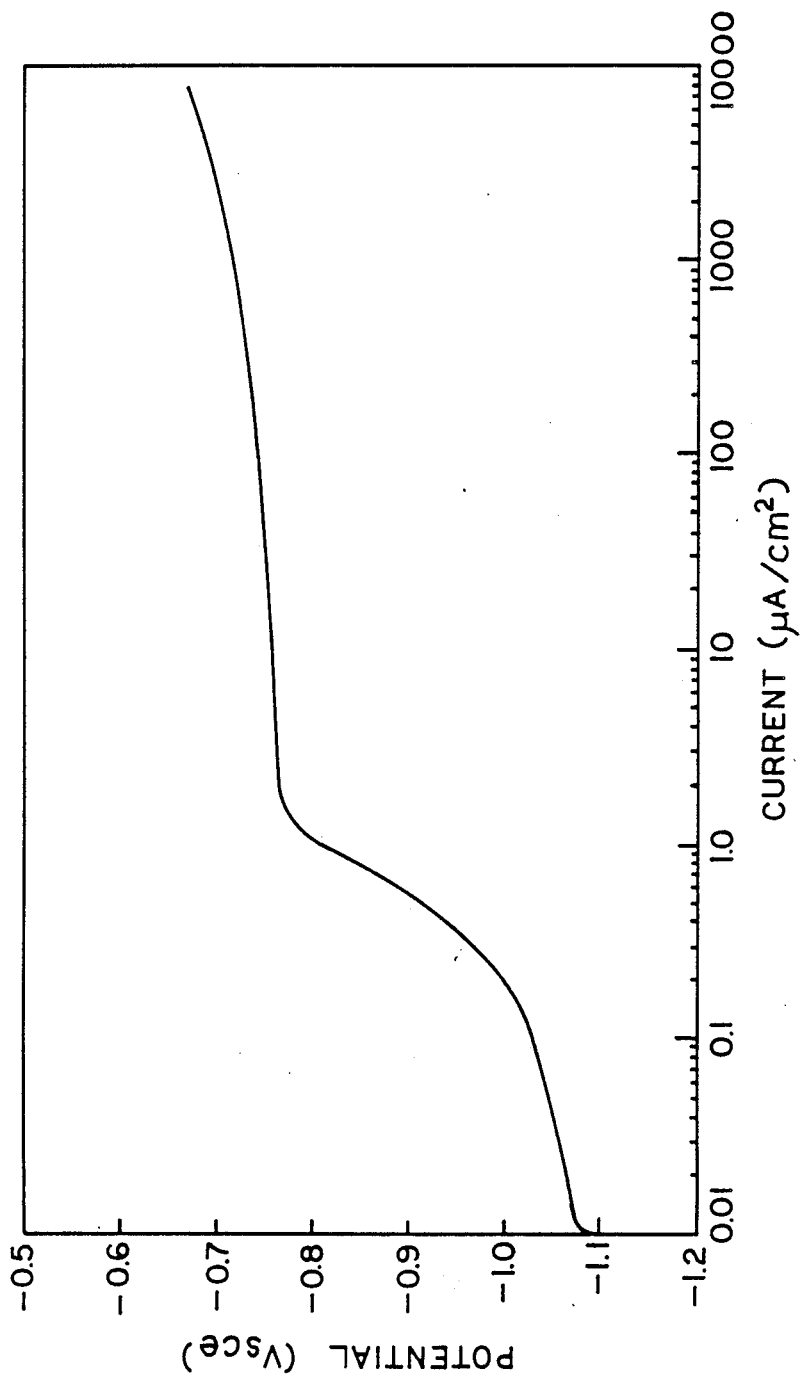

The anodic polarization curve for pure aluminum, shown in FIG. 14, exhibits active/passive tendencies. With reference to the cathodic polarization curve for DQSK steel, it may be seen that when aluminum is galvanically coupled to steel, the aluminum is in the transpassive region. The corrosion current density for aluminum is on the order of 0.02 microamps/sq.cm. This corresponds to a general corrosion rate several orders of magnitude lower than zinc.

Figure 15:
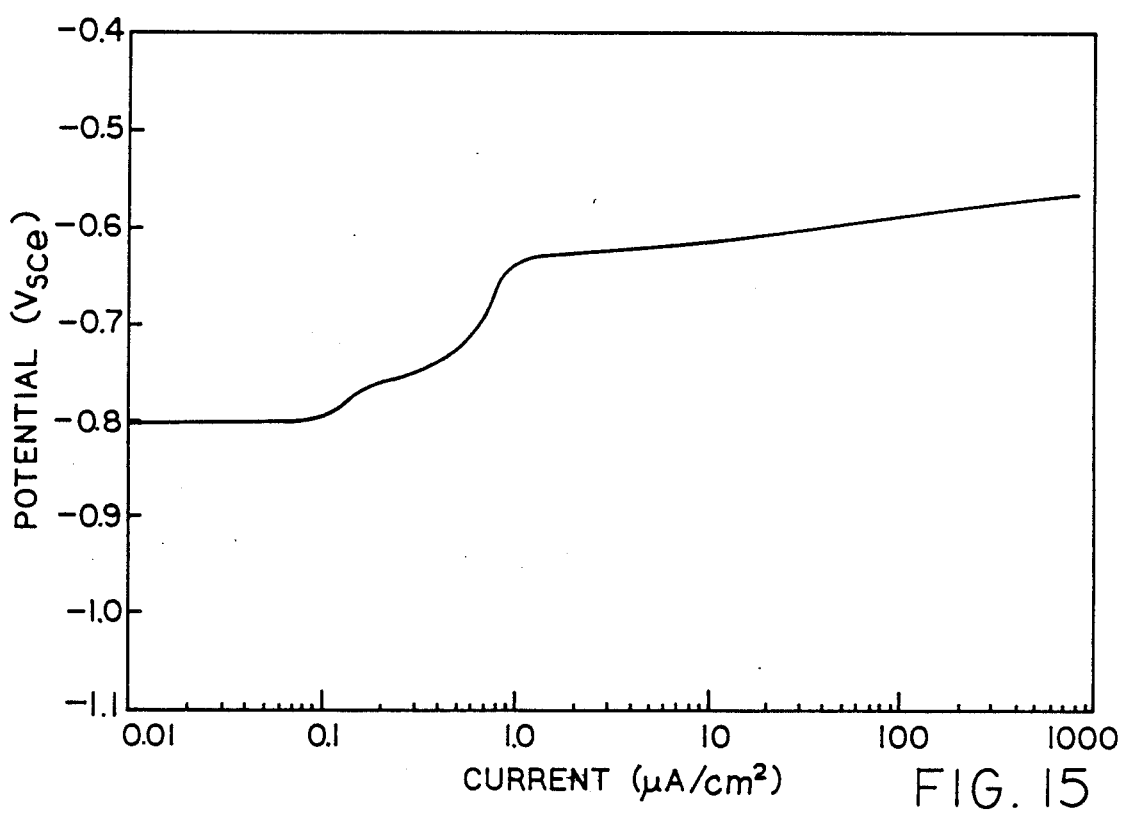

The effect of 3 weight percent magnesium on the polarization of aluminum is shown in FIG. 15. It appears that magnesium has little effect on the polarization behavior of aluminum. This system shows active/passive behavior with relatively low current densities. This alloy exhibits a general corrosion rate on the order of 0.50 microamps/sq cm.

Based on galvanic coupling experiments: (Al/3 Mg/1Si and Al/3 Mg/1 Ge) are considered to be especially useful galvanic coating alloys. Anodic polarization curves for alloys of these composition ranges are provided in FIGS. 16 and 17. For comparative purposes, the corrosion current densities for each of these alloys also is listed in Table II below.

TABLE II

| CORROSION CURRENT DENSITY OF DQSK STEEL, ALUMINUM AND SEVERAL ALUMINUM ALLOYS | | | |
|---|---|---|---|
| MATERIAL | E (mVsce) | $I_{appl}$(ma/SQ CM) | $I_{corr}$(uA/sqcm) |
| DQSK | 10 | 0.007 | 90 |
| aluminum | 15 | 0.011 | 0.02 |
| Al-Mg | 6 | 0.0001 | 0.40 |
| Al-3Mg-1Ge | 10 | 0.001 | 3 |
| Al-Mg-1Si | 8 | 0.005 | 15 |

Figure 16:
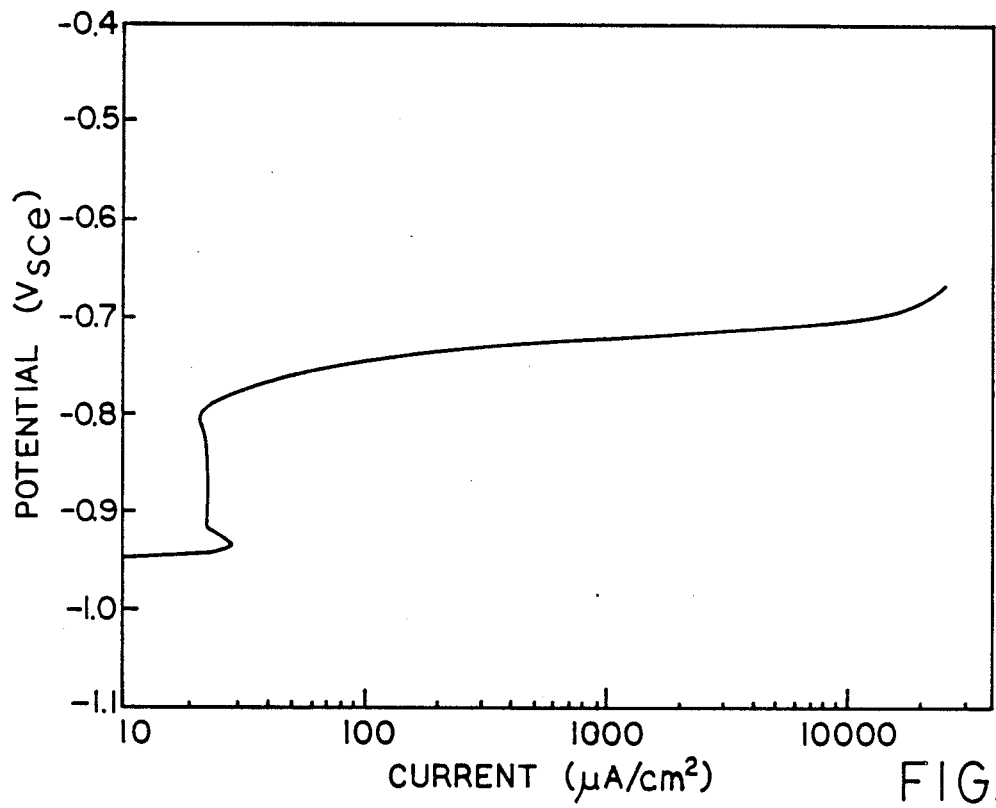
Figure 17:
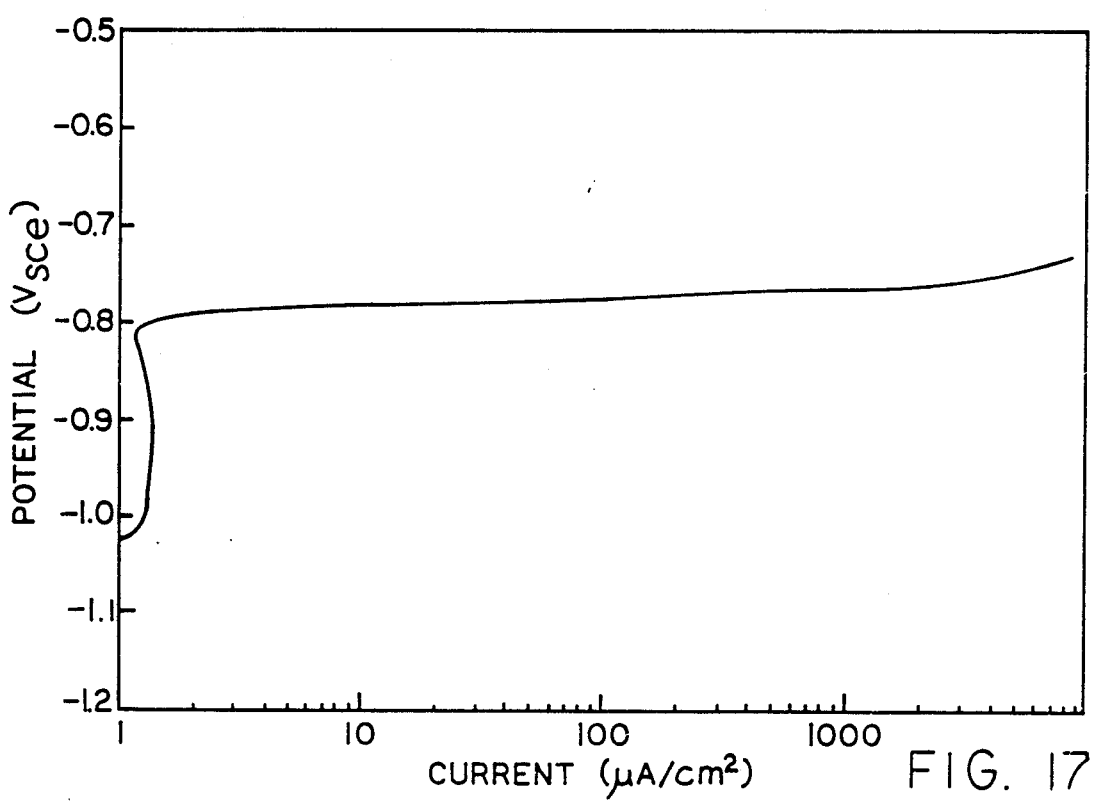

FIG. 16 displays the anodic polarization curve for Al-3Mg1Si. The current densities associated with the polarization of this alloy are about 1 order of magnitude higher than those for pure aluminum. The corrosion current density of Al-3Mg-1Si is about 15 microamps/sq om. From the polarization and galvanio coupling data it has been demonstrated that a 3% magnesium addition to aluminum-silicon alloys creates an effective galvanic coating alloy The anodic polarization of Al-3Mg-1Ge in FIG. 17 exhibits active/passive behavior. The passive current density of 2 micro-amps/sq cm corresponds to a low corrosion current density compared to zinc alloys.

It will be apparent to those skilled in the art from the foregoing that numerous improvements and changes can be made in the embodiments described of the invention without departing from the true scope of the invention. Accordingly, the foregoing disclosure is to be construed as illustrative and not in a limiting sense with the scope of the invention being defined solely by the appended claims.

We claim:

1. A method of protecting steel, other than stainless steel, from corrosion, which method comprises:

(a) coupling galvanically the steel with an alloy which consists essentially of 2.5 to 4 percent by weight magnesium, 0.5 to 3.5 percent by weight of germanium, and a balance of aluminum.

2. The method of claim 1 in which the coupling comprises a coating of the alloy on the steel.

3. The method of claim 2 which employs the alloy consisting essentially of about 3 to 3.5 percent by weight of magnesium, about 1 to 3 percent by weight of germanium, and a balance of aluminum.

4. Steel, other than stainless steel, coupled galvanically with a protective alloy consisting essentially of 2.5 to 4 percent by weight of magnesium, 0.5 to 3.5 percent by weight of silicon and a balance of aluminum, and 2.5 to 4 percent by weight of magnesium, 0.5 to 3.5 percent by weight of germanium, and a balance of aluminum.

5. The steel of claim 4 coupled by means of a coating of the alloy adhered to the steel.

6. The steel of claim 5 in which the adhered coating of the alloy consists essentially of about 3 to 3.5 percent by weight of magnesium and about 1 to 3 percent by weight of germanium, and a balance of aluminum.

7. The method of claim 1 in which the coupling galvanically is by a means providing electrical coupling.

8. The method of claim 7 in which the coupling galvanically is by means of a wire and an electrolytic solution.

9. The claim 4 steel coupled galvanically with a protective alloy in which the coupled galvanically is by a means provided electrical coupling.

10. The steel of claim 9 in which the coupled galvanically is by the means of a wire and an electrolytic solution.

* * * * *